United States Patent [19]

Dürr et al.

[11] Patent Number: 4,851,029
[45] Date of Patent: Jul. 25, 1989

[54] THIAZOLYLALKYL ESTERS OF α-IMIDAZOLINONENICOTINIC ACIDS AND HERBICIDAL METHODS OF USE

[75] Inventors: Dieter Dürr, Bottmingen; Henry Szczepanski, Wallbach, both of Switzerland

[73] Assignee: Ciba-Geigy Corporation, Hawthorne, N.Y.

[21] Appl. No.: 897,249

[22] Filed: Aug. 18, 1986

[30] Foreign Application Priority Data

Aug. 23, 1985 [CH] Switzerland .......................... 3643/85
Feb. 28, 1986 [CH] Switzerland ............................ 811/86

[51] Int. Cl.$^4$ ..................... C07D 417/14; A01N 43/50
[52] U.S. Cl. ........................................ 71/90; 546/167; 546/278; 548/204; 548/308
[58] Field of Search ................. 546/278; 71/90, 94

[56] References Cited

U.S. PATENT DOCUMENTS 4,608,079 8/1986 Los ............................................ 71/92

FOREIGN PATENT DOCUMENTS 133309 2/1985 European Pat. Off. .............. 546/82
3420271 12/1984 Fed. Rep. of Germany ...... 546/114

*Primary Examiner*—Alan L. Rotman
*Attorney, Agent, or Firm*—Kevin T. Mansfield; Edward McC. Roberts

[57] ABSTRACT

Novel thiazolylalkyl and thienylalkyl esters of α-imidazolinone-nicotinic and α-imidazolinonebenzoic acids of formula I below have good selective herbicidal properties pre- and postemergence and also influence or inhibit plant growth.

The novel esters have the formula I

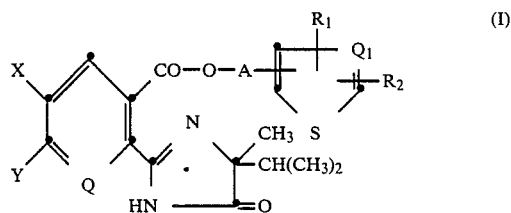

wherein
 A is a stright chain or branched $C_1$–$C_6$alkylene bridge,
 Q and $Q_1$ are each independently of the other nitrogen or the methine group,
 $R_1$ and $R_2$ are each independently of the other hydrogen or $C_1$–$C_4$alkyl, and
 X and Y are each independently of the other hydrogen, $C_1$–$C_4$alkyl, $C_1$–$C_4$alkoxy, $C_3$–$C_4$alkenyl, $C_1$–$C_4$haloalkyl or halogen, or together they are the butadiene radical.

13 Claims, No Drawings

THIAZOLYLALKYL ESTERS OF α-IMIDAZOLINONENICOTINIC ACIDS AND HERBICIDAL METHODS OF USE

The present invention relates to novel herbicidal and plant growth regulating thiazolylalkyl and thienylalkyl esters of α-imidazolinonenicotinic and α-imidazolinonebenzoic acids, as well as to the preparation of these novel compounds. The invention also relates to compositions containing the novel imidazolinone compounds, and to methods of using them for selectively controlling weeds or for regulating plant growth.

The novel thiazolylalkyl and thienylalkyl esters of α-imidazolinonenicotinic and α-imidazolinonebenzoic acids have the formula I

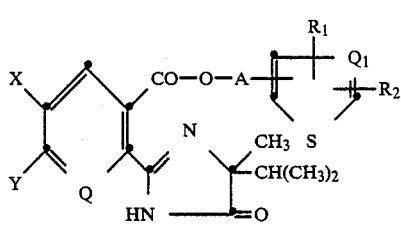

wherein

A is a straight chain or branched $C_1$–$C_6$alkylene bridge,

Q and $Q_1$ are each independently of the other nitrogen or the methine group, $R_1$ and $R_2$ are each independently of the other hydrogen or $C_1$–$C_4$alkyl, and X and Y are each independently of the other hydrogen, $C_1$–$C_4$alkyl, $C_1$–$C_4$alkoxy, $C_3$–$C_4$alkenyl, $C_1$–$C_4$haloalkyl or halogen, or together they are the butadiene radical.

In the above definitions, the alkyl and alkylene groups may be straight chain or branched, e.g. methyl, methylene, ethyl, ethylene, propyl, propylene, isopropyl, 1- or 2-methylethylene, butyl, butylene, sec-butyl, 1-methylpropylene, isobutyl, 2-methylpropylene, tert-butyl, 2,2-dimethylethylene and 1,2-dimethylethylene.

Halogen is fluorine, chlorine, bromine or iodine.

The preparation of such compounds can be represented by the following scheme:

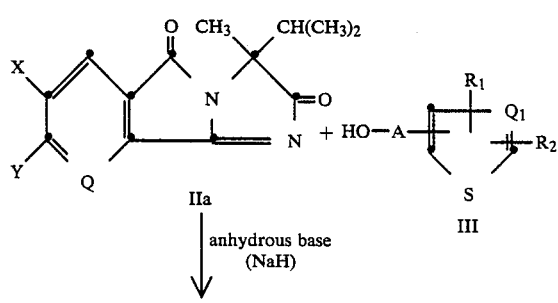

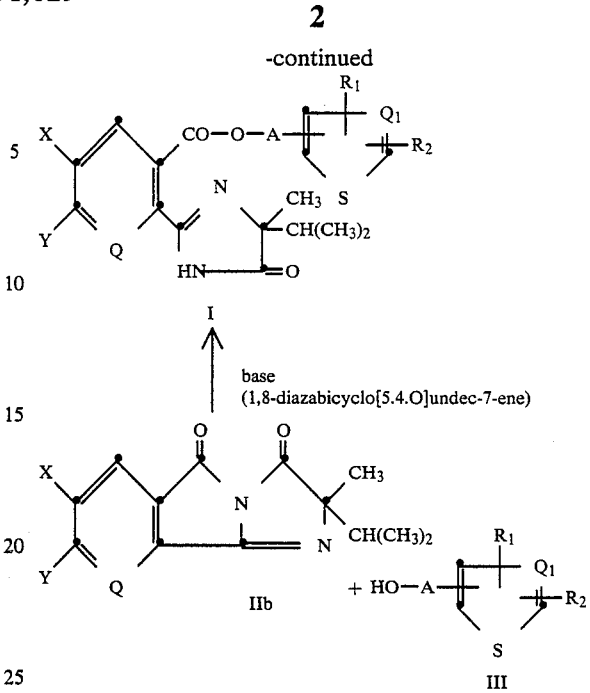

The process of the present invention for the preparation of the imidazolinone compounds of formula I comprises reacting a compound of formula IIa or IIb.

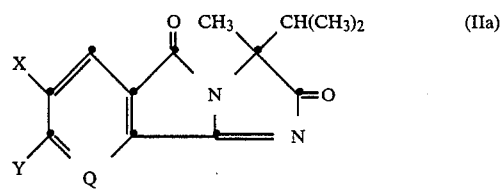

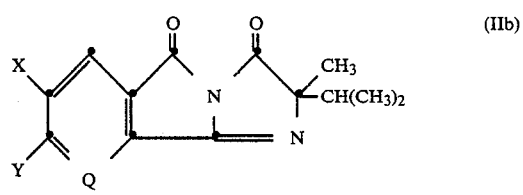

in which formulae Q, X and Y are as defined for formula I, with a thialzolyl alcohol or thienyl alcohol of formula III

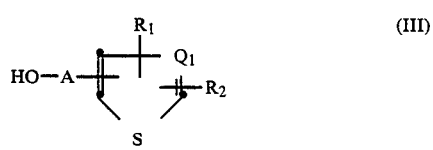

wherein A, $Q_1$, $R_1$ and $R_2$ are as defined for formula I, in an inert organic solvent or diluent and in the presence of a base.

Suitable solvents for these reactions are substantially anhydrous hydrocarbons, ethers or ketones, e.g. benzene, toluene, xylene, hexane, cyclohexane, diisopropyl ether, tetrahydrofuran and dioxane.

Examples of suitable bases are sodium hydride, 1,8-diazabicyclo[5.4.0]-undec-7-ene, tertiary amines and alkali metal hydroxides.

These reactions are carried out in the temperature range from 0° to 200° C., generally at the boiling point of the reaction mixture.

The starting materials of formula IIa are known or they can be prepared by known methods, e.g. in accordance with published European patent application 41 623 by condensing, under basic conditions, an N-(α-isopropyl-α-methylacetamido)-2,3-pyridinecarboximide or N-(α-isopropyl-α-methylacetamido)phthalimide according to the following scheme:

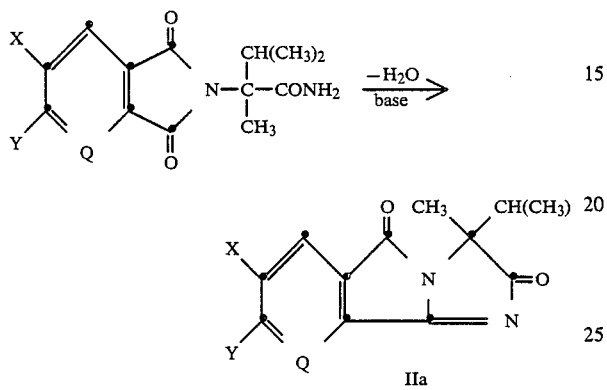

The N-(α-isopropyl-α-methylacetamido)phthalimide can be obtained by condensation of phthalic anhydride with 2-amino-(α-isopropyl-α-methylacetonitrile). The nitrile must subsequently be converted into the acid amide by heating in aqueous acid.

A pyridine-2,3-dicarboxylic acid α-isopropyl-α-methylacetamide of formula IV can be prepared in simple manner according to the following scheme by condensing an unsaturated hydrazone with a 2-chloro- or 2-bromo-N-(α-isopropyl-α-methylacetonitrile)succinimide and subsequently effecting acid hydrolysis:

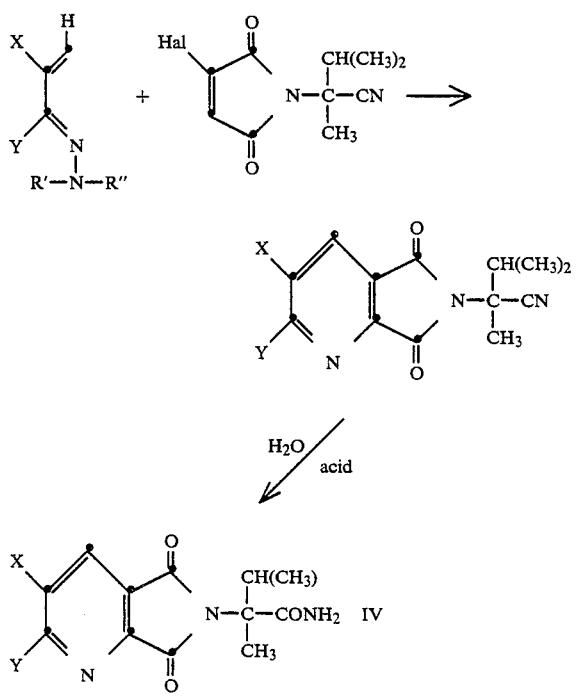

in which formulae each of R' and R" is hydrogen or $C_1$-$C_4$alkyl, Hal is chlorine or bromine, and X and Y are as defined for formula I.

The starting materials of formula IIb are obtained by converting the above N-(α-isopropyl-α-methylacetamido)-2,3-pyridinecarboximide or N-(α-isopropyl-α-methylacetamido)phthalimide, in the presence of a base such as sodium hydroxide solution, into the 2-(4-isopropyl-4-methyl-5-oxoimidazolidine)nicotinic acid derivative

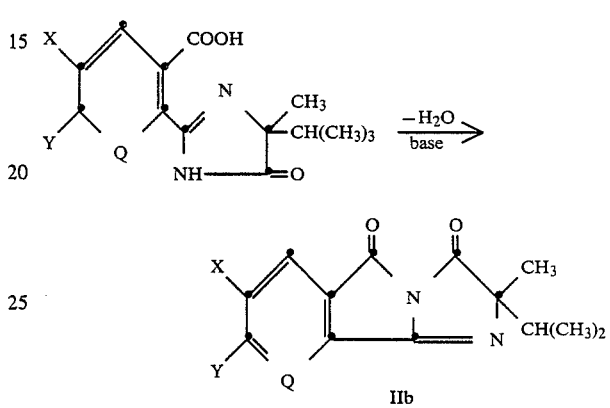

which is converted into the starting material of formula IIb (2-isopropyl-2-methyl-3H-imidazo[1',2':1,2]pyrrolo[3,4-b]pyridine-3,5-dione) by treatment with a condensing agent in an inert organic solvent, with the loss of a water molecule. Such nicotinic acid esters and the preparation thereof are described in published European patent application 41 623.

Examples of suitable condensing agents for this cyclisation are a molar amount of a strong acid, e.g. concentrated sulfuric acid, or of an anhydride, or a water absorbing reagent such as cyclohexanecarbodiimide, thionyl chloride or phosgene in the presence of a small amount of dimethylformamide. Condensation can also be effected by boiling the reaction mixture in a water separator.

If the reactions can not be carried out at room temperature, then they are carried out in the temperature range from 0° C. to 200° C., i.e. the reaction mixture is heated - if necessary - to its boiling point and cooled - if necessary - with ice/water or ice/brine.

Suitable bases for these condensation or hydrolysis reactions are in particular inorganic bases such as sodium hydroxide, sodium carbonate, sodium hydride, calcium hydroxide, calcium carbonate, potassium hydroxide, potassium carbonate, ammonia and tertiary organic bases such as triethylamine.

Suitable solvents are e.g. polar, aprotic solvents which can be used by themselves or in mixtures consisting of at least two solvents.

Among the novel esters of formula I, very active nicotinic acid esters are those in which Q and $Q_1$ are nitrogen and each of $R_1$, $R_2$, X and Y is hydrogen or $C_1$-$C_4$alkyl and which have the formula Ia

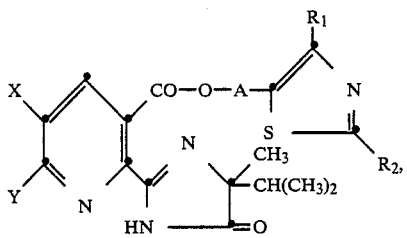

especially the compounds:
4-methylthiazol-5-ylethyl 2-(5-isopropyl-5-methyl-4-oxo-4,5-dihydroimidazolin-2-yl)nicotinate,
4-methylthiazol-5-ylethyl 5-methyl-2-(5-isopropyl-5-methyl-4-oxo-4,5-dihydroimidazolin-2-yl)nicotinate,
4-methylthiazol-5-ylethyl 5-n-propyl-2-(5-isopropyl-5-methyl-4-oxo-4,5-dihydroimidazolin-2-yl)nicotinate,
4-methylthiazol-5-ylethyl 5-isopropyl-2-(5-isopropyl-5-methyl-4-oxo-4,5-dihydroimidazolin-2-yl)nicotinate.

Those nicotinic acid thienylalkyl esters in which Q is nitrogen, $Q_1$ is the methine group and each of $R_1$, $R_2$, X and Y is hydrogen or $C_1$–$C_4$alkyl and which have the formula Ib

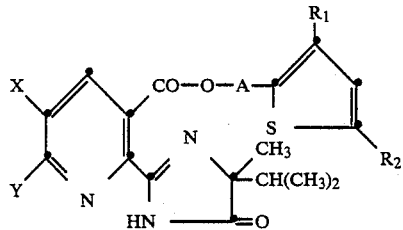

are also effective, especially
thiophen-2-ylethyl 2-(5-isopropyl-5-methyl-4-oxo-4,5-dihydroimidazolin-2-yl)nicotinate,
4-methylthiophen-2-ylethyl 5-methyl-2-(5-isopropyl-5-methyl-4-oxo-4,5-dihydroimidazolin-2-yl)nicotinate,
4-methylthiophen-2-ylethyl 5-ethyl-2-(5-isopropyl-5-methyl-4-oxo-4,5-dihydroimidazolin-2-yl)nicotinate,
4-methylthiophen-2-ylmethyl 5-methyl-2-(5-isopropyl-5-methyl-4-oxo-4,5-dihydroimidazolin-2-yl)nicotinate,
4-methylthiophen-2-ylmethyl 5-ethyl-2-(5-isopropyl-5-methyl-4-oxo-4,5-dihydroimidazolin-2-yl)nicotinate.

Those benzoic acid thiadiazolylalkyl esters in which Q is methine, $Q_1$ is nitrogen and each of $R_1$, $R_2$, X and Y is hydrogen or $C_1$–$C_4$alkyl, or X and Y together are the butadiene bridge, which esters have the formula Ic

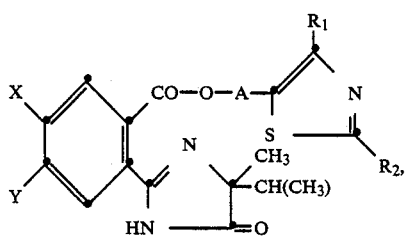

are also effective. 4-Methylthiadiazol-5-ylethyl 2-(5-isopropyl-5-methyl-4-oxo-4,5-dihydroimidazolin-2-yl)benzoate is particularly effective.

Good activity is exhibited by those benzoic or naphthoic acid thienylalkyl esters in which Q and $Q_1$ are methine, each of $R_1$, $R_2$, X and Y is hydrogen or $C_1$–$C_4$alkyl, or X and Y together are the butadiene bridge, which esters have the formula Ie

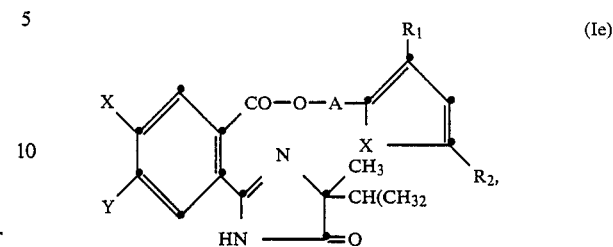

and also by those 3-quinolinic acid thiazolylalkyl and thienylalkyl esters in which Q is nitrogen, $Q_1$ is nitrogen or methine, each of $R_1$ and $R_2$ is hydrogen or $C_1$–$C_4$alkyl and X and Y together form the butadiene bridge, which esters have the formula If

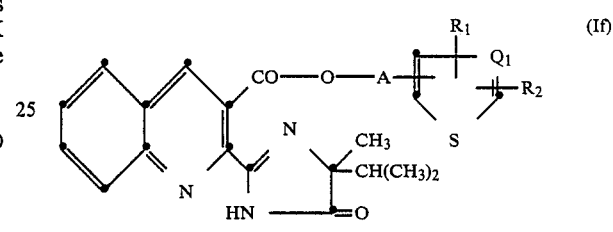

The invention relates to all diastereomeric and enantiomeric isomers of the compounds of formula I.

The compounds of formula I are usually successfully applied at concentrations of 0.05 to 4 kg/ha, in particular 0.1 to 1 kg/ha.

When used at low rates of application, the compounds of formula I have good selective growth inhibiting and selective herbicidal properties which make them most suitable for use in crops of useful plants, preferably in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced growth inhibiting properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, New Jersey, 1981; H. Stache, "Tensid-Taschenbuch" (Handbook of Surfactants), C. Hanser Verlag, Munich & Vienna, 1981.

The compositions usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| compound of formula I | 1 to 20%, preferably 5 to 10% |
| surfactant | 5 to 30%, preferably 10 to 20% |
| liquid carrier | 50 to 94%, preferably 70 to 85% |
| Dusts | |
| compound of formula I | 0.1 to 10%, preferably 0.1 to 1% |
| solid carrier | 99.9 to 90%, preferably 99.9 to 99% |
| Suspension concentrates | |
| compound of formula I | 5 to 75%, preferably 10 to 50% |
| water | 94 to 25%, preferably 90 to 30% |
| surfactant | 1 to 40%, preferably 2 to 30% |
| Wettable powders | |
| compound of formula I | 0.5 to 90%, preferably 1 to 80% |
| surfactant | 0.5 to 20%, preferably 1 to 15% |
| solid carrier | 5 to 95%, preferably 15 to 90% |
| Granulates | |
| compound of formula I | 0.5 to 30%, preferably 3 to 15% |
| solid carrier | 99.5 to 70%, preferably 97 to 85% |

Whereas commercial products will be preferably formulated as concentrates, the end user will normally employ dilute formulations. The formulations can be diluted to a concentration as low as 0.001% of active ingredient. The rates of application are usually from 0.005 to 5 kg a.i./ha.

The compositions may also contain further ingredients such as stabilisers, antifoams, viscosity regulators, binders, tackifiers, as well as fertilisers and other compounds for obtaining special effects.

The preparation of a number of compounds of formula I is illustrated by the following Examples. Further compounds prepared in corresponding manner are listed in the subsequent Tables.

EXAMPLE 1

Preparation of 4-methylthiazol-5-ylethyl 2-(5-isopropyl-5-methyl-4-oxo-4,5-dihydroimidazolin-2-yl)nicotinate

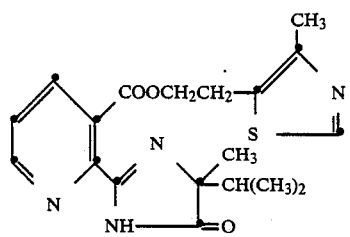

A mixture of 9 g of 3,5-dioxo-2-isopropyl-2-methyl-2,3-dihydroimidazo[1',2':1,2]-5-H-pyrrolo[3,4-b]pyridine in 50 ml of tetrahydrofuran, 5.5 g of 5-(2-hydroxyethyl)-4-methylthiazole and 2 drops of 1,8-diazabicyclo[5.4.0]undec-7-ene is boiled under reflux for 3 hours in a sulfurating flask. The solvent is then evaporated off in vacuo and the initially oily residue is triturated with 50 ml of ether, whereupon 7.7 g of the product crystalline. A further portion can be obtained by concentration of the mother liquor and crystallisation from acetone/ether. The crystals melt at 154°–157° C. Yield: 8.5 g.

The 3,5-dioxo-2-isopropyl-2-methyl-2,3-dihydroimidazo[1',2':1,2]-5-H-pyrrolo[3,4-b]pyridine required as starting material is prepared as follows:

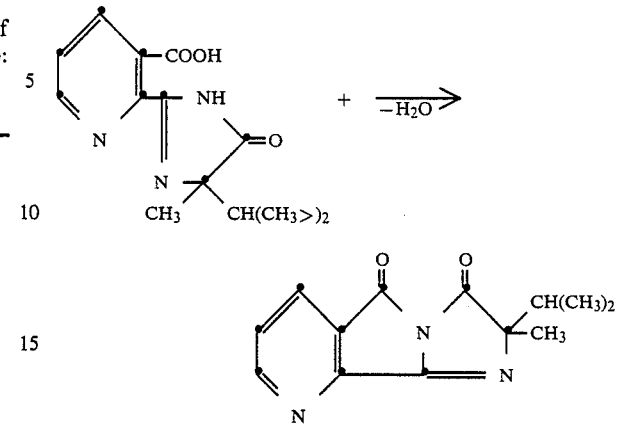

With stirring, 15.6 g (0.05 mole) of 2-(5-isopropyl-5-methyl)-2-oxo-2-imidazolin-2-ylnicotinic acid are added to a solution of 11.1 g of dicyclohexylcarbodiimide in 100 ml of methylene chloride. Stirring is continued for a further 2 hours at room temperature. The resultant dicyclohexylurea is removed by suction filtration and the residue is washed with a small amount of methylene chloride. The filtrate is concentrated by evaporation and the residue is then recrystallised from ethyl acetate/hexane, affording the title product in 91% yield (12.1 g) in the form of crystals which melt at 132°–133° C.

The following starting materials are obtained in analogous manner

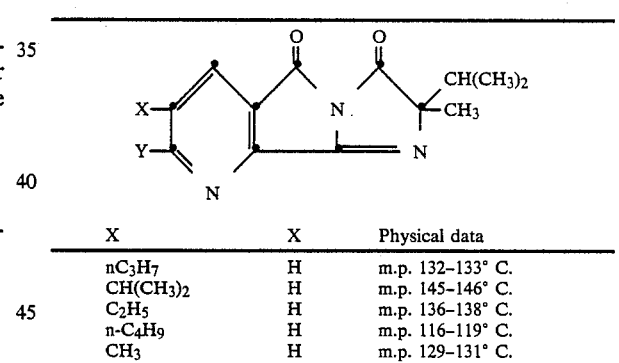

| X | X | Physical data |
|---|---|---|
| nC₃H₇ | H | m.p. 132–133° C. |
| CH(CH₃)₂ | H | m.p. 145–146° C. |
| C₂H₅ | H | m.p. 136–138° C. |
| n-C₄H₉ | H | m.p. 116–119° C. |
| CH₃ | H | m.p. 129–131° C. |

EXAMPLE 2

Preparation of thienyl-2-ylethyl 2-(5-isopropyl-5-methyl-4-oxo-4,5-dihydroimidazolin-2-yl)nicotinate

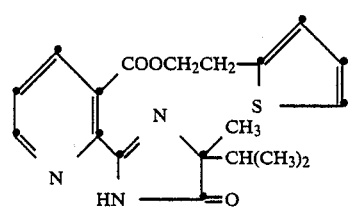

Under a nitrogen atmosphere, one gram of sodium hydride (80% in white oil) is slowly added to a solution of 10 g of 2-(2-thienyl)ethanol in 100 ml of dry toluene. After 15 minutes 10 g of 3-isopropyl-3-methyl-3H-imidazo[1',2':1,2]pyrrolo[3,4-b]pyridine-2,5-dione are added and the mixture is then heated under reflux for 1 hour. For working up, the reaction mixture is concentrated by evaporation in vacuo and the residue is chromatographed through a column of silica gel (elution with a 1:2 mixture of tetrahydrofuran and petroluem ether). The first fractions contains excess thienylethanol. The product is isolated in the form of a pale oil from the succeeding fractions after concentrating by evaporation and drying in vacuo. The wall of the vessel containing the pale oil is scratched with a glass rod, causing said oil to crystallise. Yield: 9 g of title product which melts at 84°–87° C.

The 3-isopropyl-3-methyl-3H-imidazo[1',2':1,2]pyrrolo[3,4-b]pyridine-2,5-dione required as starting material is prepared as follows:

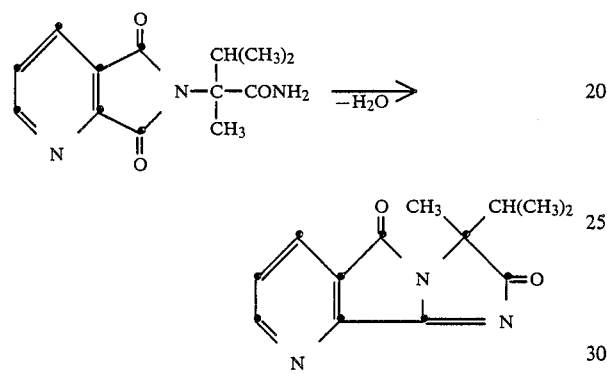

With the simultaneous addition of 0.5 g of powdered sodium hydroxide, a solution of 5,7-dihydro-α-isopropyl-α-methyl-5,7-dioxo-6H-pyrrolo[3,4-b]pyridine-6-acetamide (m.p.: 82° C.) in 100 ml of toluene is heated under reflux for 2 hours in a water separator. After the reaction solution has cooled, it is filtered through silica gel and the filtrate is washed with ethyl acetate and then concentrated by evaporation. The residue is recrystallised from ethyl acetate/petroleum ether, affording 13.1 g of the title compound which melts at 116° C.

The following starting materials are obtained in analogous manner.

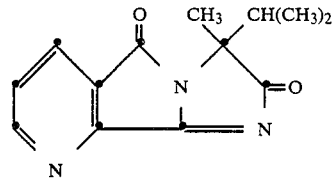

| X | Y | Physical data |
|---|---|---|
| nC₃H₇ | H | m.p. 116° C. |
| C₂H₅ | H | m.p. 119–120° C. |
| n-C₄H₉ | H | m.p. 86–87° C. |
| CH(CH₃)₂ | H | |
| CH₃ | H | m.p. 102–106° C. |
| —(CH=CH)₂— | H | |
| H | CH₃ | |
| CH₃ | CH₃ | |
| CH(CH₃)C₂H₅ | H | |

The compounds listed in the following Tables are obtained by following a procedure analogous to that of Examples 1 and 2 using corresponding starting materials.

TABLE 1

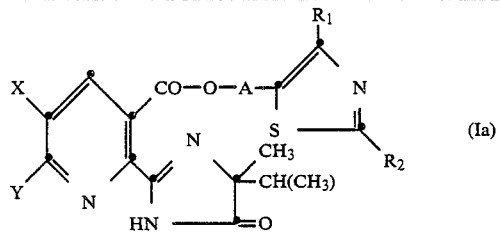

(Ia)

| Comp. | —A— | X | Y | R₁ | R₂ | Physical data |
|---|---|---|---|---|---|---|
| 1.01 | —C₂H₄— | H | H | CH₃ | H | m.p. 154–157° C. Example 1 |
| 1.02 | —C₂H₄— | CH₃ | H | CH₃ | H | m.p. 103–105° C. |
| 1.03 | —C₂H₄— | C₂H₅ | H | CH₃ | H | m.p. 97–99° C. |
| 1.04 | —C₂H₄— | C₃H₇—n | H | CH₃ | H | m.p. 107–110° C. |
| 1.05 | —C₂H₄— | —(CH=CH)₂— | H | CH₃ | H | m.p. 148–150° C. |
| 1.06 | —C₂H₄— | H | H | CH₃ | CH₃ | |
| 1.07 | —C₂H₄— | H | H | C₂H₅ | H | |
| 1.08 | —C₂H₄— | CH₃ | H | H | H | |
| 1.09 | —C₂H₄— | C₂H₅ | H | H | H | |
| 1.10 | —C₂H₄— | CH₃ | H | H | CH₃ | |
| 1.11 | —C₂H₄— | C₂H₅ | H | H | CH₃ | |
| 1.12 | —C₂H₄— | —(CH=CH)₂— | | CH₃ | CH₃ | |
| 1.13 | —C₂H₄— | H | CH₃ | CH₃ | H | |
| 1.14 | —C₂H₄— | C₃H₇—i | H | CH₃ | H | |
| 1.15 | —C₂H₄— | C₄H₉—n | H | CH₃ | H | |
| 1.16 | —C₂H₄— | CH₃ | H | CH₃ | CH₃ | |
| 1.17 | —C₂H₄— | —(CH=CH)₂— | | CH₃ | C₂H₅ | |
| 1.18 | —C₂H₄— | H | CH₃ | H | H | |
| 1.19 | —C₂H₄— | H | C₂H₅ | H | H | |
| 1.20 | —C₂H₄— | H | H | H | H | |
| 1.21 | —C₂H₄— | H | CH₃ | C₂H₅ | H | |
| 1.22 | —C₂H₄— | H | H | C₂H₅ | CH₃ | |
| 1.23 | —CH₂— | H | H | CH₃ | H | |
| 1.24 | —CH₂— | CH₃ | H | CH₃ | H | |
| 1.25 | —CH₂— | C₂H₅ | H | CH₃ | H | |
| 1.26 | —CH₂— | C₃H₇—n | H | CH₃ | H | |

TABLE 1-continued

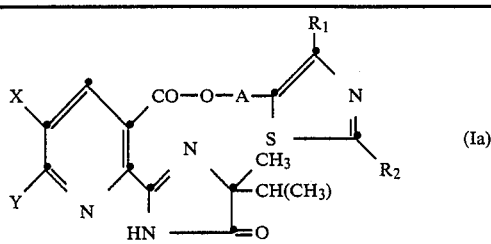

(Ia)

| Comp. | —A— | X | Y | $R_1$ | $R_2$ | Physical data |
|---|---|---|---|---|---|---|
| 1.27 | —CH$_2$— | —(CH=CH)$_2$— | | CH$_3$ | H | |
| 1.28 | —CH$_2$— | H | H | CH$_3$ | CH$_3$ | |
| 1.29 | —CH$_2$— | H | H | C$_2$H$_5$ | H | |
| 1.30 | —CH$_2$— | CH$_3$ | H | H | H | |
| 1.31 | —CH$_2$— | C$_2$H$_5$ | H | H | H | |
| 1.32 | —CH$_2$— | —(CH=CH)$_2$— | | H | CH$_3$ | |
| 1.33 | —CH$_2$— | H | CH$_3$ | H | CH$_3$ | |
| 1.34 | —CH$_2$— | C$_3$H$_7$—i | H | CH$_3$ | CH$_3$ | |
| 1.35 | —CH$_2$— | C$_4$H$_9$—n | H | CH$_3$ | H | |
| 1.36 | —CH$_2$— | CH$_3$ | H | CH$_3$ | H | |
| 1.37 | —CH$_2$— | —(CH=CH)$_2$— | | H | H | |
| 1.38 | —CH$_2$— | H | CH$_3$ | CH$_3$ | CH$_3$ | |
| 1.39 | —CH$_2$— | H | C$_2$H$_5$ | CH$_3$ | C$_2$H$_5$ | |
| 1.40 | —CH$_2$— | H | CH$_3$ | H | H | |
| 1.41 | —CH$_2$— | H | C$_2$H$_5$ | H | H | |
| 1.42 | —CH$_2$— | H | H | H | H | |
| 1.43 | —CH$_2$— | H | CH$_3$ | C$_2$H$_5$ | H | |
| 1.44 | —CH$_2$— | H | H | C$_2$H$_5$ | CH$_3$ | |
| 1.45 | —CH$_2$— | Br | H | H | H | |
| 1.46 | —CH$_2$— | H | C$_3$H$_7$i | H | H | |
| 1.47 | —CH$_2$— | Cl | H | H | H | |
| 1.48 | —CH$_2$— | —CH=CCl—CH=CH— | | H | H | |
| 1.49 | —CH$_2$— | H | CH(CH$_3$)$_2$ | H | H | |
| 1.50 | —C$_2$H$_4$— | H | H | H | H | |
| 1.51 | —C$_2$H$_4$— | —CH=CH)$_2$— | | H | H | |
| 1.52 | —C$_2$H$_4$— | Cl | H | H | H | |
| 1.53 | —C$_2$H$_4$— | —CH=CCl—CH=CH— | | H | H | |
| 1.54 | —C$_2$H$_4$— | Br | H | H | H | |

TABLE 2

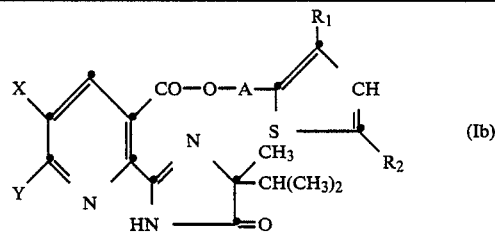

(Ib)

| Comp. | —A— | X | Y | $R_1$ | $R_2$ | Physical data |
|---|---|---|---|---|---|---|
| 2.01 | —C$_2$H$_4$— | H | H | H | H | m.p. 84–87° C. Example 2 |
| 2.02 | —C$_2$H$_4$— | CH$_3$ | H | H | H | m.p. 110–112° C. |
| 2.03 | —C$_2$H$_4$— | C$_2$H$_5$ | H | H | H | m.p. 75–78° C. |
| 2.04 | —C$_2$H$_4$— | C$_3$H$_7$-n | H | CH$_3$ | H | |
| 2.05 | —C$_2$H$_4$— | —(CH=CH)$_2$— | | CH$_3$ | H | |
| 2.06 | —C$_2$H$_4$— | H | H | CH$_3$ | CH$_3$ | |
| 2.07 | —C$_2$H$_4$— | H | H | C$_2$H$_5$ | H | |
| 2.08 | —C$_2$H$_4$— | —(CH=CH)$_2$— | | H | H | |
| 2.09 | —C$_2$H$_4$— | C$_3$H$_7$i | H | H | H | |
| 2.10 | —C$_2$H$_4$— | CH$_3$ | H | H | CH$_3$ | |
| 2.11 | —C$_2$H$_4$— | C$_2$H$_5$ | H | H | CH$_3$ | |
| 2.12 | —C$_2$H$_4$— | —(CH=CH)$_2$— | | CH$_3$ | CH$_3$ | |
| 2.13 | —C$_2$H$_4$— | H | CH$_3$ | CH$_3$ | H | |
| 2.14 | —C$_2$H$_4$— | C$_3$H$_7$—i | H | CH$_3$ | H | |
| 2.15 | —C$_2$H$_4$— | C$_4$H$_9$—n | H | CH$_3$ | H | |
| 2.16 | —C$_2$H$_4$— | CH$_3$ | H | CH$_3$ | CH$_3$ | |
| 2.17 | —C$_2$H$_4$— | —(CH=CH)$_2$— | | CH$_3$ | C$_2$H$_5$ | |
| 2.18 | —C$_2$H$_4$— | H | CH$_3$ | H | H | m.p. 115–116° C. |
| 2.19 | —C$_2$H$_4$— | H | C$_2$H$_5$ | H | H | |
| 2.20 | —C$_2$H$_4$— | —CH=CCl—CH=CH$_2$— | H | H | H | |
| 2.21 | —C$_2$H$_4$— | H | CH$_3$ | C$_2$H$_5$ | H | |
| 2.22 | —C$_2$H$_4$— | H | H | C$_2$H$_5$ | CH$_3$ | |

TABLE 2-continued

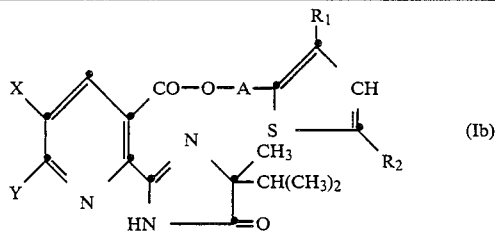

(Ib)

| Comp. | —A— | X | Y | R₁ | R₂ | Physical data |
|---|---|---|---|---|---|---|
| 2.23 | —CH₂— | H | H | H | H | m.p. 126–127° C. |
| 2.24 | —CH₂— | CH₃ | H | H | H | m.p. 121–123° C. |
| 2.25 | —CH₂— | C₂H₅ | H | H | H | m.p. 87–88.5° C. |
| 2.26 | —CH₂— | C₃H₇—n | H | CH₃ | H | |
| 2.27 | —CH₂— | —(CH=CH)₂— | | CH₃ | H | |
| 2.28 | —CH₂— | H | H | CH₃ | CH₃ | |
| 2.29 | —CH₂— | H | H | C₂H₅ | H | |
| 2.30 | —CH₂— | Cl | H | H | H | |
| 2.31 | —CH₂— | —(CH=CH)₂— | | H | CH₃ | |
| 2.32 | —CH₂— | CH₃ | H | H | CH₃ | |
| 2.33 | —CH₂— | C₂H₅ | H | H | CH₃ | |
| 2.34 | —CH₂— | —(CH=CH)₂— | | CH₃ | CH₃ | |
| 2.35 | —CH₂— | H | CH₃ | CH₃ | H | |
| 2.36 | —CH₂— | C₃H₇—i | H | CH₃ | H | |
| 2.37 | —CH₂— | C₄H₉—n | H | CH₃ | H | |
| 2.38 | —CH₂— | CH₃ | H | CH₃ | CH₃ | |
| 2.39 | —CH₂— | —(CH=CH)₂— | | CH₃ | C₂H₅ | |
| 2.40 | —CH₂— | H | CH₃ | H | H | |
| 2.41 | —CH₂— | H | C₂H₅ | H | H | |
| 2.42 | —CH₂— | H | H | H | H | |
| 2.43 | —CH₂— | H | CH₃ | C₂H₅ | H | |
| 2.44 | —CH₂— | H | H | C₂H₅ | CH₃ | |
| 2.45 | —CH₂— | —(CH=CH₂)₂— | | H | CH₃ | |
| 2.46 | —CH₂— | Br | H | H | CH₃ | |
| 2.47 | —CH₂— | Cl | H | H | CH₃ | |
| 2.48 | —CH₂— | —CH=CCl—CH=CH— | H | CH₃ | | |
| 2.49 | —CH₂— | H | C₃H₇i | H | CH₃ | |
| 2.50 | —CH₂— | —(CH=CH)₂ | | H | H | m.p. 136–137° C. |
| 2.51 | —CH₂— | Cl | H | H | H | |
| 2.52 | —CH₂— | —CH=CCl—CH=CH₂— | H | H | | |
| 2.53 | —CH₂— | Br | H | | H | |
| 2.54 | —CH₂— | H | CH(CH₃)₂ | H | H | |
| 2.55 | —CH(C₃H₇n)— | H | H | H | H | |
| 2.56 | —CH(C₃H₇n)— | CH₃ | H | H | H | |
| 2.57 | —CH(C₃H₇n)— | C₂H₅ | H | H | H | |
| 2.58 | —CH(C₃H₇n)— | —(CH=CH)₂— | | H | H | |
| 2.59 | —CH(C₃H₇n)— | Cl | H | H | H | |
| 2.60 | —CH(C₃H₇n)— | —CH=CCl—CH=CH— | H | H | | |
| 2.61 | —CH(C₃H₇n)— | Br | H | H | H | |
| 2.62 | —CH(C₃H₇n)— | H | CH(CH₃)₂ | H | H | |
| 2.63 | —CH(CH₃)— | H | H | H . | H | |
| 2.64 | —CH(CH₃)— | CH₃ | H | H | H | |
| 2.65 | —CH(CH₃)— | C₂H₅ | H | H | H | |
| 2.66 | —CH(CH₃)₂— | —(CH=CH)₂— | | H | H | |
| 2.67 | —CH(CH₃)₂— | Cl | H | H | H | |
| 2.68 | —CH(CH₃)₂— | —CH=CCl—CH=CH— | | H | H | |
| 2.69 | —CH(CH₃)₂— | Br | H | H | H | |
| 2.70 | —CH(CH₃)₂— | H | CH(CH₃)₂ | H | H | |
| 2.71 | —CH₂— | H | H | H | CH₃ | |
| 2.72 | —(CH₂)₃— | H | H | H | H | |
| 2.73 | —CH₂CH₂— | Br | H | H | H | |
| 2.74 | —CH₂CH₂ | Cl | H | H | H | |
| 2.75 | —C₂H₄— | Br | H | H | H | |
| 2.76 | —C₂H₄— | H | CH(CH₃)₂ | H | H | |
| 2.77 | —(CH₂)₃— | H | H | H | H | |
| 2.78 | —(CH₂)₃— | CH₃ | H | H | H | |
| 2.79 | —(CH₂)₃— | C₂H₅ | H | H | H | |
| 2.80 | —(CH₂)₃— | —(CH=CH)₂— | | H | H | |
| 2.81 | —(CH₂)₃— | Cl | H | H | H | |
| 2.82 | —(CH₂)₃— | —CH=CCl—CH=CH— | | H | H | |
| 2.83 | —(CH₂)₃— | Br | H | H | H | |
| 2.84 | —(CH₂)₃— | H | CH(CH₃)₂ | H | H | |
| 2.85 | —CH₂— | CH₃ | H | H | CH₃ | |
| 2.86 | —CH₂— | C₂H₅ | H | H | CH₃ | |
| 2.87 | —CH₂— | —(CH=CH)₂— | | H | CH₃ | |
| 2.88 | —CH₂— | —CH=CCl—CH=CH— | | H | CH₃ | |
| 2.89 | —CH₂— | Br | H | H | CH₃ | |

TABLE 2-continued

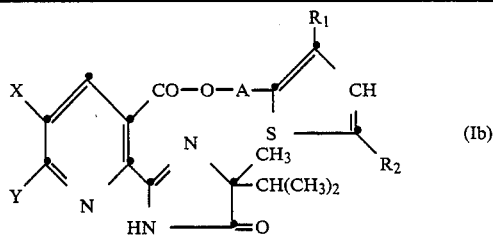

(Ib)

| Comp. | —A— | X | Y | $R_1$ | $R_2$ | Physical data |
|---|---|---|---|---|---|---|
| 2.90 | —CH$_2$— | H | | CH(CH$_3$)$_2$ | H | CH$_3$ |

TABLE 3

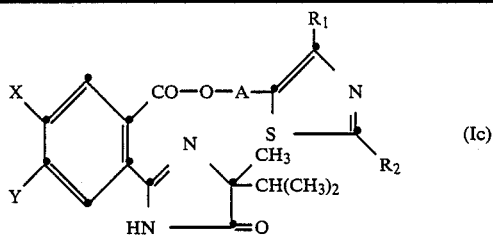

(Ic)

| Comp. | —A— | X | Y | $R_1$ | $R_2$ | Physical data |
|---|---|---|---|---|---|---|
| 3.01 | —C$_2$H$_4$— | H | H | CH$_3$ | H | oil$_D^{25}$ = 1.5624 |
| 3.02 | —C$_2$H$_4$— | CH$_3$ | H | CH$_3$ | H | |
| 3.03 | —C$_2$H$_4$— | C$_2$H$_5$ | H | CH$_3$ | H | |
| 3.04 | —C$_2$H$_4$— | C$_3$H$_7$—n | H | CH$_3$ | H | |
| 3.05 | —C$_2$H$_4$— | —(CH=CH)$_2$— | | CH$_3$ | H | |
| 3.06 | —C$_2$H$_4$— | H | H | CH$_3$ | CH$_3$ | |
| 3.07 | —C$_2$H$_4$— | H | H | C$_2$H$_5$ | H | |
| 3.08 | —C$_2$H$_4$— | CH$_3$ | H | H | H | |
| 3.09 | —C$_2$H$_4$— | C$_2$H$_5$ | H | H | H | |
| 3.10 | —C$_2$H$_4$— | CH$_3$ | H | H | CH$_3$ | |
| 3.11 | —C$_2$H$_4$— | C$_2$H$_5$ | H | H | CH$_3$ | |
| 3.12 | —C$_2$H$_4$— | —(CH=CH)$_2$— | | CH$_3$ | CH$_3$ | |
| 3.13 | —C$_2$H$_4$— | H | CH$_3$ | CH$_3$ | H | |
| 3.14 | —C$_2$H$_4$— | C$_3$H$_7$—i | H | CH$_3$ | H | |
| 3.15 | —C$_2$H$_4$— | C$_4$H$_9$—n | H | CH$_3$ | H | |
| 3.16 | —C$_2$H$_4$— | CH$_3$ | H | CH$_3$ | CH$_3$ | |
| 3.17 | —C$_2$H$_4$— | —(CH=CH)$_2$— | | CH$_3$ | C$_2$H$_5$ | |
| 3.18 | —C$_2$H$_4$— | H | CH$_3$ | H | H | |
| 3.19 | —C$_2$H$_4$— | H | C$_2$H$_5$ | H | H | |
| 3.20 | —C$_2$H$_4$— | H | H | H | H | |
| 3.21 | —C$_2$H$_4$— | H | CH$_3$ | C$_2$H$_5$ | H | |
| 3.22 | —C$_2$H$_4$— | H | H | C$_2$H$_5$ | CH$_3$ | |
| 3.23 | —CH$_2$— | H | H | CH$_3$ | H | |
| 3.24 | —CH$_2$— | H | CH$_3$ | H | | |
| 3.25 | —CH$_2$— | C$_2$H$_5$ | H | CH$_3$ | H | |
| 3.26 | —CH$_2$— | C$_3$H$_7$—n | H | CH$_3$ | H | |
| 3.27 | —CH$_2$— | —CH=CCl—CH=CH— | | CH$_3$ | H | |
| 3.28 | —CH$_2$— | H | H | CH$_3$ | CH$_3$ | |
| 3.29 | —CH$_2$— | H | H | C$_2$H$_5$ | H | |
| 3.30 | —CH$_2$— | CH$_3$ | H | H | H | |
| 3.31 | —CH$_2$— | C$_2$H$_5$ | H | H | H | |
| 3.32 | —CH$_2$— | CH$_3$ | H | H | CH$_3$ | |
| 3.33 | —CH$_2$— | C$_2$H$_5$ | H | H | CH$_3$ | |
| 3.34 | —CH$_2$— | —(CH=CH)$_2$— | | CH$_3$ | CH$_3$ | |
| 3.35 | —CH$_2$— | H | CH$_3$ | CH$_3$ | H | |
| 3.36 | —CH$_2$— | C$_3$H$_7$—i | H | CH$_3$ | H | |
| 3.37 | —CH$_2$— | C$_4$H$_9$—n | H | CH$_3$ | H | |
| 3.38 | —CH$_2$— | CH$_3$ | H | CH$_3$ | CH$_3$ | |
| 3.39 | —CH$_2$— | —(CH=CH)$_2$— | | CH$_3$ | C$_2$H$_5$ | |
| 3.40 | —CH$_2$— | H | CH$_3$ | H | H | |
| 3.41 | —CH$_2$— | H | C$_2$H$_5$ | H | H | |
| 3.42 | —CH$_2$— | H | H | H | H | |
| 3.43 | —CH$_2$— | H | CH$_3$ | C$_2$H$_5$ | H | |
| 3.44 | —CH$_2$— | H | H | C$_2$H$_5$ | CH$_3$ | |
| 3.45 | —CH$_2$— | —(CH=CH)$_2$— | | H | H | |
| 3.46 | —CH$_2$— | Br | H | H | H | |
| 3.47 | —CH$_2$— | Cl | H | H | H | |

TABLE 3-continued

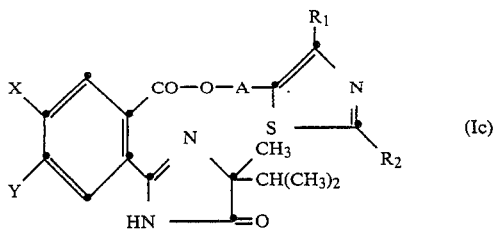

(Ic)

| Comp. | —A— | X | Y | R₁ | R₂ | Physical data |
|---|---|---|---|---|---|---|
| 3.48 | —CH₂— | —CH=CH—CH=CH— (Cl) | | H | H | |
| 3.49 | —CH₂— | H | CH(CH₃)₂ | H | H | |
| 3.50 | —CH₂— | H | H | H | CF₃ | |
| 3.51 | —CH₂— | CH₃ | H | H | CF₃ | |
| 3.52 | —CH₂— | C₂H₅ | H | H | CF₃ | |
| 3.53 | —CH₂— | —(CH=CH)₂— | | H | CF₃ | |
| 3.54 | —CH₂— | Cl | H | H | H | |
| 3.55 | —CH₂— | —CH=CCl—CH=CH— | | H | H | |
| 3.56 | —CH₂— | Br | H | H | H | |
| 3.57 | —CH₂— | H | CH(CH₃)₂ | H | H | |
| 3.58 | —CH₂CH₂— | Br | H | CH₃ | H | |
| 3.59 | —CH₂CH₂— | —CH=CCl—CH=CH— | | CH₃ | H | |
| 3.60 | CH₂ | Br | H | CH₃ | H | |
| 3.61 | CH₂ | —CH=CCl—CH=CH— | | CH₃ | H | |

TABLE 4

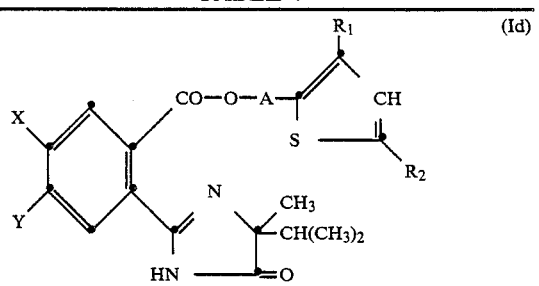

(Id)

| Comp. | —A— | X | Y | R₁ | R₂ | Physical data |
|---|---|---|---|---|---|---|
| 4.01 | —C₂H₄— | H | H | H | H | m.p. 103–105° C. |
| 4.02 | —C₂H₄— | CH₃ | H | CH₃ | H | |
| 4.03 | —C₂H₄— | C₂H₅ | H | CH₃ | H | |
| 4.04 | —C₂H₄— | C₃H₇—n | H | CH₃ | H | |
| 4.05 | —C₂H₄— | —CH₂=CH)₂— | | CH₃ | H | |
| 4.06 | —C₂H₄— | H | H | CH₃ | CH₃ | |
| 4.07 | —C₂H₄— | H | H | C₂H₅ | H | |
| 4.08 | —C₂H₄— | CH₃ | H | H | H | |
| 4.09 | —C₂H₄— | C₂H₅ | H | H | H | |
| 4.10 | —C₂H₄— | CH₃ | H | H | CH₃ | |
| 4.11 | —C₂H₄— | C₂H₅ | H | H | CH₃ | |
| 4.12 | —C₂H₄— | —(CH=CH)₂— | | CH₃ | CH₃ | |
| 4.13 | —C₂H₄— | H | CH₃ | H | H | |
| 4.14 | —C₂H₄— | C₃H₇—i | H | CH₃ | H | |
| 4.15 | —C₂H₄— | C₄H₉—n | H | CH₃ | H | |
| 4.16 | —C₂H₄— | CH₃ | H | CH₃ | CH₃ | |
| 4.17 | —C₂H₄— | —(CH=CH)₂— | | CH₃ | C₂H₅ | |
| 4.18 | —C₂H₄— | H | CH₃ | H | H | |
| 4.19 | —C₂H₄— | H | C₂H₅ | H | H | |
| 4.20 | —C₂H₄— | H | H | H | H | |
| 4.21 | —C₂H₄— | H | CH₃ | C₂H₅ | H | |
| 4.22 | —C₂H₄— | H | H | C₂H₅ | CH₃ | |

TABLE 4-continued

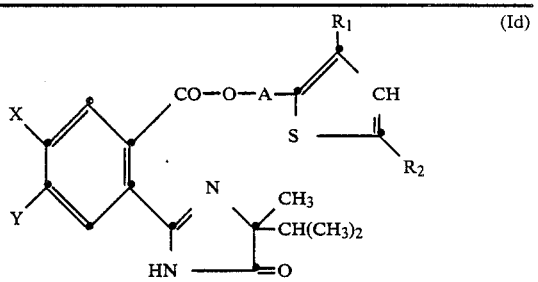

(Id)

| Comp. | —A— | X | Y | R₁ | R₂ | Physical data |
|---|---|---|---|---|---|---|
| 4.23 | —CH₂— | H | H | H | H | |
| 4.24 | —CH₂— | CH₃ | H | CH₃ | H | |
| 4.25 | —CH₂— | C₂H₅ | H | CH₃ | H | |
| 4.26 | —CH₂— | C₃H₇—n | H | CH₃ | H | |
| 4.27 | —CH₂— | —CH₂=CH)₂— | | CH₃ | H | |
| 4.28 | —CH₂— | H | H | CH₃ | CH₃ | |
| 4.29 | —CH₂— | H | H | C₂H₅ | H | |
| 4.30 | —CH₂— | CH₃ | H | H | H | |
| 4.31 | —CH₂— | C₂H₅ | H | H | H | |
| 4.32 | —CH₂— | CH₃ | H | H | CH₃ | |
| 4.33 | —CH₂— | C₂H₅ | H | H | CH₃ | |
| 4.34 | —CH₂— | —(CH=CH)₂— | | CH₃ | CH₃ | |
| 4.35 | —CH₂— | H | CH₃ | CH₃ | H | |
| 4.36 | —CH₂— | C₃H₇—i | H | CH₃ | H | |
| 4.37 | —CH₂— | C₄H₉—n | H | CH₃ | H | |
| 4.38 | —CH₂— | CH₃ | H | CH₃ | CH₃ | |
| 4.39 | —CH₂— | —(CH=CH)₂— | | CH₃ | C₂H₅ | |
| 4.40 | —CH₂— | H | CH₃ | H | H | |
| 4.41 | —CH₂— | H | C₂H₅ | H | H | |
| 4.42 | —CH₂— | H | H | H | H | |
| 4.43 | —CH₂— | H | CH₃ | C₂H₅ | H | |
| 4.44 | —CH₂— | H | H | C₂H₅ | CH₃ | |

TABLE 5

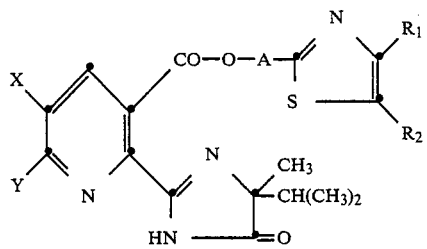

| Comp. | —A— | X | Y | $R_1$ | $R_2$ | Physical data |
|---|---|---|---|---|---|---|
| 5.01 | —CH$_2$— | H | H | H | CH$_3$ | |
| 5.02 | —CH$_2$— | CH$_3$ | H | H | CH$_3$ | |
| 5.03 | —CH$_2$— | C$_2$H$_5$ | H | H | CH$_3$ | |
| 5.04 | —CH$_2$— | —(CH=CH)$_2$— | | H | CH$_3$ | |
| 5.05 | —CH$_2$— | Cl | H | H | CH$_3$ | |
| 5.06 | —CH$_2$— | —CH=CCl—CH=CH— | | H | CH$_3$ | |
| 5.07 | —CH$_2$— | Br | H | H | CH$_2$ | |
| 5.08 | —CH$_2$— | H | CH(CH$_3$)$_2$ | H | CH$_2$ | |
| 5.09 | —CH(C$_3$H$_7$n)— | H | H | H | H | |
| 5.10 | —CH(C$_3$H$_7$n)— | CH$_3$ | H | H | H | |
| 5.11 | —CH$_3$(C$_3$H$_7$n)— | C$_2$H$_5$ | H | H | H | |
| 5.12 | —CH(C$_3$H$_7$n)— | —(CH=CH)$_2$— | | H | H | |
| 5.13 | —CH(C$_3$H$_7$n)— | Cl | H | H | H | |
| 5.14 | —CH(C$_3$H$_7$n)— | —CH=CCl—CH=CH— | | H | H | |
| 5.15 | —CH(C$_3$H$_7$n)— | Br | H | H | H | |
| 5.16 | —CH(C$_3$H$_7$n)— | H | CH(CH$_3$)$_2$ | H | H | |
| 5.17 | —C$_2$H$_4$— | H | H | H | H | |
| 5.18 | —C$_2$H$_4$— | CH$_3$ | H | H | H | |
| 5.19 | —C$_2$H$_4$— | C$_2$H$_5$ | H | H | H | |
| 5.20 | —C$_2$H$_4$— | —(CH=CH)$_2$— | | H | H | |
| 5.21 | —C$_2$H$_4$— | Cl | H | H | H | |
| 5.22 | —C$_2$H$_4$— | —CH=CCl—CH=CH— | | H | H | |
| 5.23 | —C$_2$H$_4$— | Br | H | H | H | |
| 5.24 | —C$_2$H$_4$— | H | CH(CH$_3$)$_2$ | H | H | |
| 5.25 | —CH$_2$— | H | H | H | H | |
| 5.26 | —CH$_2$— | CH$_3$ | H | H | H | |
| 5.27 | —CH$_2$— | C$_2$H$_5$ | H | H | H | |
| 5.28 | —CH$_2$— | —(CH=CH)$_2$— | | H | H | |
| 5.29 | —CH$_2$— | Cl | H | H | H | |
| 5.30 | —CH$_2$— | —CH=CCl—CH=CH— | | H | H | |
| 5.31 | —CH$_2$— | Br | H | H | H | |
| 5.32 | —CH$_2$— | H | CH(CH$_3$)$_2$ | H | H | |
| 5.33 | —CH(C$_2$H$_5$)— | H | H | H | H | |
| 5.34 | —CH(C$_2$H$_5$)— | CH$_3$ | H | H | H | |
| 5.35 | —CH(C$_2$H$_5$)— | C$_2$H$_5$ | H | H | H | |
| 5.36 | —CH(C$_2$H$_5$)— | Cl | H | H | H | |
| 5.37 | —CH(C$_2$H$_5$)— | —CH=CCl—CH=CH— | | H | H | |
| 5.38 | —CH(C$_2$H$_5$)— | Br | H | H | H | |
| 5.39 | —CH(C$_2$H$_5$)— | H | CH(CH$_3$)$_2$ | H | H | |
| 5.40 | —CH(C$_2$H$_5$)— | —(CH=CH)$_2$— | | H | H | |

TABLE 6

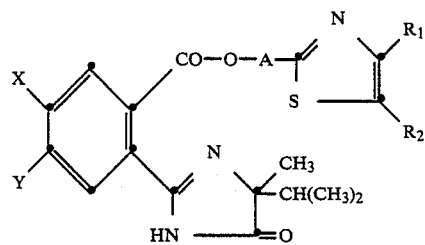

| Comp. | —A— | X | Y | $R_1$ | $R_2$ | Physical data |
|---|---|---|---|---|---|---|
| 6.01 | —CH$_2$— | H | H | H | H | |
| 6.02 | —CH$_2$— | CH$_3$ | H | H | H | |
| 6.03 | —CH$_2$— | C$_2$H$_5$ | H | H | H | |
| 6.04 | —CH$_2$— | —(CH=CH)$_2$— | | H | H | |
| 6.05 | —CH$_2$— | Cl | H | H | H | |
| 6.06 | —CH$_2$— | —CH=CCl—CH=CH— | | H | H | |
| 6.07 | —CH$_2$— | Br | H | H | H | |
| 6.08 | —CH$_2$— | H | CH(CH$_3$)$_2$ | H | H | |
| 6.09 | —C$_2$H$_4$— | H | H | H | H | |
| 6.10 | —C$_2$H$_4$— | CH$_3$ | H | H | H | |

TABLE 6-continued

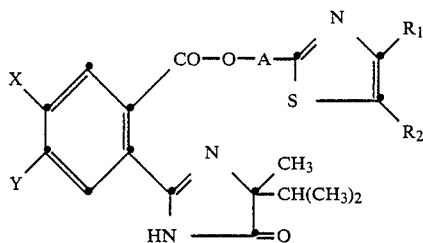

| Comp. | —A— | X | Y | $R_1$ | $R_2$ | Physical data |
|---|---|---|---|---|---|---|
| 6.11 | —$C_2H_4$— | $C_2H_5$ | H | H | H | |
| 6.12 | —$C_2H_4$— | Cl | H | H | H | |
| 6.13 | —$C_2H_4$— | —CH=CCl—CH=CH— | | H | H | |
| 6.14 | —$C_2H_4$— | Br | H | H | H | |
| 6.15 | —$C_2H_4$— | H | $CH(CH_3)_2$ | H | H | |
| 6.16 | —$C_2H_4$— | —(CH=CH)$_2$— | | H | H | |
| 6.17 | —$(CH_2)_3$— | H | H | H | H | |
| 6.18 | —$(CH_2)_3$— | $CH_3$ | H | H | H | |
| 6.19 | —$(CH_2)_3$— | $C_2H_5$ | H | H | H | |
| 6.20 | —$(CH_2)_3$— | —(CH=CH)$_2$— | | H | H | |
| 6.21 | —$(CH_2)_3$— | Cl | H | H | H | |
| 6.22 | —$(CH_2)_3$— | —CH=CCl—CH=CH— | | H | H | |
| 6.23 | —$(CH_2)_3$— | Br | H | H | H | |
| 6.24 | —$(CH_2)_3$— | H | $CH(CH_3)_2$ | H | H | |
| 6.25 | —$CH_2$— | H | H | H | $CH_3$ | |
| 6.26 | —$CH_2$— | $CH_3$ | H | H | $CH_3$ | |
| 6.27 | —$CH_2$— | $C_2H_5$ | H | H | $CH_3$ | |
| 6.28 | —$CH_2$— | —(CH=CH)$_2$— | | H | $CH_3$ | |
| 6.29 | —$CH_2$— | Cl | H | H | H | |
| 6.30 | —$CH_2$— | CH=CCl—CH=CH— | | H | $CH_3$ | |
| 6.31 | —$CH_2$— | Br | H | H | $CH_3$ | |
| 6.32 | —$CH_2$— | H | $CH(CH_3)_2$ | H | $CH_3$ | |

Formulation Examples

EXAMPLE 3

Formulation Examples for compounds of formula I (percentages are by weight)

| (a) Wettable powders | (a) | (b) | (c) |
|---|---|---|---|
| compound of Tables 1 to 6 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| compound of Tables 1 to 6 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of Tables 1 to 6 | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulates | (a) | (b) |
|---|---|---|
| compound of Tables 1 to 6 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of Tables 1 to 6 | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrates | (a) | (b) |
|---|---|---|
| compound of Tables 1 to 6 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of Tables 1 to 6 | 5% |
| isopropylamine | 1% |
| octylphenol polyethylene glycol ether (78 moles of ethylene oxide) | 3% |
| water | 91% |

Biological Examples

EXAMPLE 4

Preemergence herbicidal action

In a greenhouse, immediately after sowing the test plants in seed dishes, the surface of the soil is treated with an aqueous dispersion of the test compounds, obtained from a 25% emulsifiable concentrate. Concentrations of 4 kg of test compound per hectare are applied. The seed dishes are kept in the greenhouse at 22°–25° C. and 50% relative humidity. The test is evaluated 3 weeks later in accordance with the following rating:
1 plant has not germinated or it has died
2–3 very severe damage
4 severe damage
5 moderate damage, stunted growth
6 damage, the plant can regenerate
7–8 slight damage
9 normal growth, as untreated plants In this test, the compounds of Tables 1 to 6 exhibit strong herbicidal activity. A number of results are given in Table 7.

TABLE 7

| Compound | Avena | Setaria | Sinapsis | Stellaria |
|---|---|---|---|---|
| 1.01 | 2 | 1 | 2 | 2 |
| 2.01 | 2 | 2 | 1 | 2 |
| 3.01 | 2 | 1 | 2 | 2 |

EXAMPLE 5

Postemergence herbicidal action (contact herbicide)

A number of weeds, both mono- and dicotyledonous, are sprayed postemergence in the 4- to 6-leaf stage with an aqueous active ingredient dispersion at a rate of 4 kg of test compound per hectare and kept at 24°–26° C. and 45–60% relative humidity. The test is evaluated 15 days later in accordance with the same rating as employed above. In this test, the compounds of Tables 1 to 6 also exhibit strong to very strong herbicidal activity. A number of results are given in Table 8.

TABLE 8

| Compound | Avena | Setaria | Lolium | Solanum | Sinapsis | Stellaria |
|---|---|---|---|---|---|---|
| 1.01 | 1 | 3 | 1 | 1 | 2 | 2 |
| 2.01 | 1 | 2 | 2 | 1 | 2 | 2 |
| 3.02 | 1 | 2 | 2 | 1 | 1 | 2 |

EXAMPLE 6

Preemergence herbicidal action

Plastic pots are filled with expanded vermiculite (density: 0.135 g/cm$^3$; water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 klux and a relative humidity of 70%. During the germinating phase of 4 to 6 days, the pots are covered with lightpermeable material and watered with deionised water to increase the local humidity. After the 5th day, 0,5% of a commercial liquid fertiliser (Greenzit ®) is added to the water. The test is evaluated 12 days after sowing and the action on the plants is assessed in accordance with the rating indicated in Example 4.

The results are given in Table 9:

TABLE 9

| Compound | Rate of application ppm | Nasturtium officinalis | Agrostis tenuis | Stellaria media | Digitaria sang. |
|---|---|---|---|---|---|
| 1.01 | 100 | 1 | 1 | 1 | 1 |
|  | 10 | 2 | 2 | 1 | 1 |
|  | 1 | 3 | 2 | 1 | 3 |
|  | 0.1 | 4 | 4 | 2 | 3 |
|  | 0.01 | 4 | 4 | 5 | 6 |
| 2.01 | 100 | 2 | 2 | 2 | 2 |
|  | 10 | 2 | 2 | 2 | 2 |
|  | 1 | 2 | 2 | 2 | 2 |
|  | 0.1 | 3 | 3 | 3 | 3 |
|  | 0.01 | 3 | 3 | 3 | 3 |
| 3.01 | 100 | 2 | 2 | 2 | 2 |
|  | 10 | 4 | 5 | 4 | 4 |

EXAMPLE 8

Herbicidal action in wild rice (paddy)

The weeds *Echinocloa crus galli* and *Monocharia vag.*, which occur in water, are sown in plastic beakers (surface: 60 cm$^2$; volume: 500 ml). After sowing, the beakers are filled with water up to the surface of the soil. 3 days after sowing, the water level is increased to slightly above the soil surface (3–5 mm). Application is effected 3 days after sowing by spraying the beakers with an aqueous emulsion of the test compounds. The rate of application corresponds to a concentration of 4 kg of active ingredient per hectare (concentration of the spray mixture=550 l/ha). The beakers are then kept in the greenhouse under optimum growth conditions for rice weeds, i.e. at 25°–30° C. and at high humidity. The evaluation of the tests takes place 3 weeks after application.

The test compounds of Tables 1 to 6 exhibit good activity in this test.

EXAMPLE 9

Growth inhibition of tropical leguminous cover crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test, a marked reduction in new growth of the plants treated with compounds of Tables 1 to 6 at concentrations of 50 to 3000 g/ha is observed (less than 20% of the new growth of untreated control plants), without damage being caused to the test plants.

EXAMPLE 10

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of Tables 1 to 6 of the invention markedly increase the number and weight of the harvested siliquae on the leading shoot.

EXAMPLE 11

Growth inhibition of cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of Tables 1 to 6. The concentration corresponds to up to 100 g of active ingredient per hectare. Evaluation of the growth of the cereals is made 21 days after application. A comparison with untreated controls shows that the new growth of treated cereal plants is reduced (60-90% of the controls) and that the diameter of the stalks has in some cases increased.

EXAMPLE 12

Growth inhibition of grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of Tables 1 to 6. The concentration of test compound corresponds to a rate of application of up to 500 g a.i. per hectare. The growth of the grasses is evaluated 21 days after application. The test compounds effect a reduction in new growth in the range of 10-30% in comparison with untreated controls.

EXAMPLE 13

Desiccation and defoliation action

Cotton plants of the Deltapine variety are reared in earthen-ware pots in a greenhouse. After the capsules have formed, the plants are sprayed with an aqueous formulation of a compound of Tables 1 to 6 at rates of application corresponding to 1.2, 0.6 and 0.3 kg/ha in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant).

In this test, plants treated with test compounds of Tables 1 to 6 at rates of application of 0.6 and 1.2 kg/ha are left after 7 days with only a few dried out leaves (<80% defoliation and dessication).

What is claimed is:

1. A thiazolylalkyl ester of an α-imidazolinonenicotinic or acid of formula I

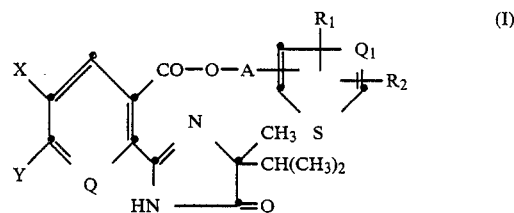

wherein
A is a straight chain or branched $C_1$-$C_6$alkylene bridge, Q is nitrogen, $Q_1$ is nitrogen,
$R_1$ and $R_2$ are each independently of the other hydrogen or $C_1$-$C_4$alkyl, and
X and Y are each independently of the other hydrogen, $C_1$-$C_4$alkyl, $C_1$-$C_4$alkoxy, $C_3$-$C_4$alkenyl, $C_1$-$C_4$haloalkyl or halogen.

2. An α-imidazolinonenicotinic acid 2-thiazolylalkyl ester according to claim 1 of formula Ia

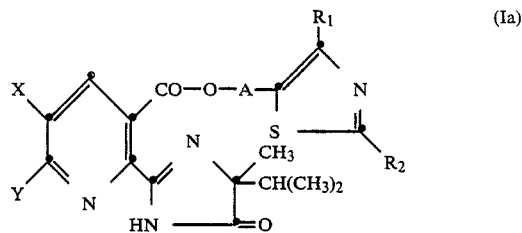

wherein each of $R_1$, $R_2$, X and Y is hydrogen or $C_1$-$C_4$alkyl.

3. 4-Methylthiazol-5-ylethyl 2-(5-isopropyl-5-methyl-4-oxo-4,5-dihydroimidazolin-2-yl)nicotinate according to claim 1.

4. 4-Methylthiazol-5-ylethyl 5-methyl-2-(5-isopropyl-5-methyl-4-oxo-4,5-dihydroimidazolin-2-yl)nicotinate according to claim 1.

5. 4-Methylthiazol-5-ylethyl 5-n-propyl-2-(5-isopropyl-b 5-methyl-4-oxo-4,5-dihydroimidazolin-2-yl)nicotinate according to claim 1.

6. 4-Methylthiazol-5-ylethyl 5-isopropyl-2-(5-isopropyl-5-methyl-4-oxo-4,5-dihydroimidazolin-2-yl)nicotinate according to claim 1.

7. A herbicidal composition which comprises, as active ingredient, a herbicidally effective amount of a 2-thiazolylalkyl ester of a 2-alphaimidazolinonenicotinic acid according to claim 1, together with a carrier or other adjuvant.

8. A method of controlling undesired plant growth, which method comprises applying a herbicidally effective amount of a compound according to claim 1 to the undesired plants or their loci.

9. A method of inhibiting plant growth, which method comprises applying a herbicidally effective amount of a compound according to claim 1 to the plants or their loci.

10. A method of influencing plant growth for increasing the yield, which method comprises applying a yield-increasingly effective amount of a compound according to claim 1 to the plants or their loci.

11. A method of selectively controlling weeds pre- or postemergence in crops of useful plants, which method comprises treating said useful plants or the crop areas thereof with a herbicidally effective amount of an imidazolinone compound of formula I according to claim 1.

12. A method of suppressing plant growth beyond the 2-leaf stage, which method comprises treating the plants during their growth with a growth suppressingly effective amount of an imidazolinone compound of formula I according to claim 1.

13. A plant growth regulating composition which comprises, as active ingredient, a growth-regulatingly effective amount of a 2-thiazolylakyl ester of a 2-alpha-imidazolinonenicotinic acid according to claim 1, together with a carrier or other adjuvant.

* * * * *